United States Patent
Mallory et al.

[11] Patent Number: 6,129,825
[45] Date of Patent: *Oct. 10, 2000

[54] ELECTROCHEMICAL GAS SENSOR

[75] Inventors: John Mallory, Mississauga; Wenfeng Peng, North York, both of Canada

[73] Assignee: Senco Sensors Inc., Vancouver, Canada

[*] Notice: This patent issued on a continued prosecution application filed under 37 CFR 1.53(d), and is subject to the twenty year patent term provisions of 35 U.S.C. 154(a)(2).

[21] Appl. No.: 08/939,669

[22] Filed: Sep. 29, 1997

[30] Foreign Application Priority Data

Sep. 11, 1997 [CA] Canada ................... 2215108

[51] Int. Cl.$^7$ ................... G01N 27/404
[52] U.S. Cl. ............ 204/415; 204/432; 205/783
[58] Field of Search ............. 204/415, 431, 204/432; 95/901

[56] References Cited

U.S. PATENT DOCUMENTS

| | | | |
|---|---|---|---|
| 3,029,576 | 4/1962 | Collins | 95/901 |
| 3,429,796 | 2/1969 | Lauer | 204/415 |
| 3,668,101 | 6/1972 | Bergman | 204/415 |
| 3,755,125 | 8/1973 | Shaw et al. | 204/415 |
| 4,025,412 | 5/1977 | LaConti . | |
| 4,141,800 | 2/1979 | Brever et al. | 204/415 |
| 4,169,779 | 10/1979 | Tataria et al. | 204/415 |
| 4,227,984 | 10/1980 | Dempsey et al. . | |
| 4,394,239 | 7/1983 | Kitzelmann et al. . | |
| 4,406,770 | 9/1983 | Chan et al. | 204/415 |
| 4,522,690 | 6/1985 | Venkatasetty . | |
| 4,543,273 | 9/1985 | Handa et al. . | |
| 4,587,003 | 5/1986 | Tantram et al. . | |
| 4,633,704 | 1/1987 | Tantram et al. | 204/415 |
| 5,024,682 | 6/1991 | Turk | 95/901 |
| 5,173,166 | 12/1992 | Tomantschger et al. . | |
| 5,246,576 | 9/1993 | Leader et al. | 204/415 |
| 5,284,566 | 2/1994 | Cuomo et al. . | |
| 5,302,274 | 4/1994 | Tomantschger et al. | 204/415 |
| 5,338,429 | 8/1994 | Jolson et al. . | |
| 5,628,890 | 5/1997 | Carter et al. | 204/415 |
| 5,656,069 | 8/1997 | Nikolskaja et al. | 95/901 |

FOREIGN PATENT DOCUMENTS

| | | |
|---|---|---|
| 0 293 230 A2 | 11/1988 | European Pat. Off. . |
| 0 762 116 A1 | 3/1997 | European Pat. Off. . |
| WO 96 14576 | 5/1996 | WIPO . |

*Primary Examiner*—T. Tung
*Attorney, Agent, or Firm*—Libert & Associates; Victor E. Libert

[57] ABSTRACT

A simple, reliable, and leak-proof electrochemical sensor for detection of toxic gases. The sensor comprises a housing having an electrochemical gas sensor cell with an electrolyte and first and second electrodes bonded to conductive plastic. Each of the first and second electrodes is a membrane formed from a fluoropolymer film having a layer adhered thereto of a catalyst-impregnated fluoropolymer. The layers of each of said first and second electrodes are bonded to conductive plastic, and are separated by an absorbent material having an electrolyte absorbed therein. The sensor is particularly intended for detection of carbon monoxide, but may be used to detect other gases.

18 Claims, 4 Drawing Sheets

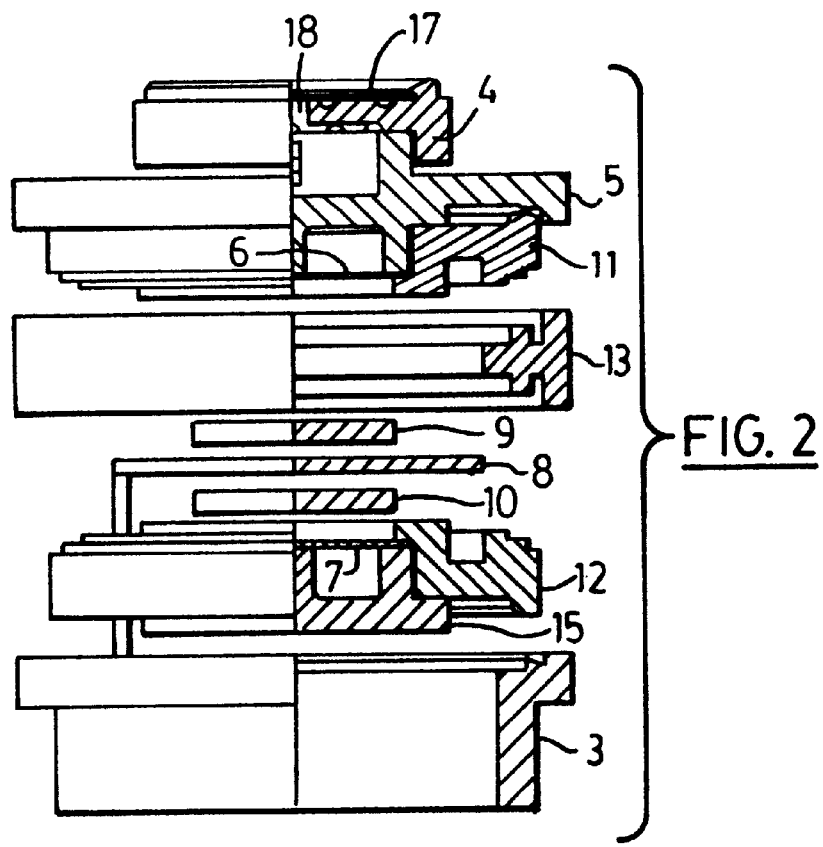
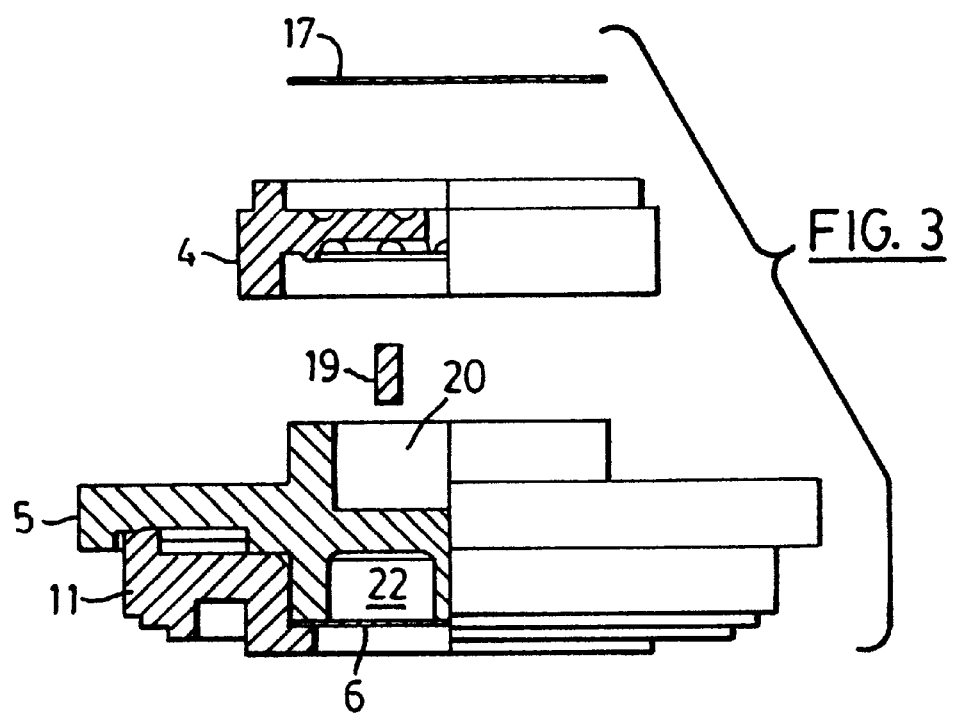

ELECTROCHEMICAL GAS SENSOR

FIELD OF THE INVENTION

The present invention relates to an electrochemical gas sensor, especially an electrochemical gas sensor used in the monitoring of the presence of a gas in an atmosphere that might contain the gas e.g. the presence of the gas in air. In preferred embodiments, the gas is carbon monoxide, but the sensor may be used to detect other gases, as described below. Nonetheless, the invention will be described herein with particular reference to detection of carbon monoxide.

BACKGROUND OF THE INVENTION

There are three principal methods of detecting the presence of carbon monoxide (CO) in air. The first method of detection uses a plug-in detector having a periodically-heated semi-conductor that exhibits a change in conductivity when CO is present. However, this type of detector requires AC-power, and ceases to function when electricity to the unit fails. The detector tends to be sensitive to changes in humidity, and is cross-sensitive to the presence of other combustible gases e.g. alcohols, including materials containing alcohols, examples of which include hairspray.

The second type of detector uses a translucent gel disk that darkens on prolonged exposure to CO. The change in translucency is detected by an infrared sensor within the unit. Detection tends to be less responsive than for other detectors, taking hours rather than minutes to recover after the ambient air has become free of CO. Consequently, it becomes necessary to remove the battery-sensor pack in order to silence the alarm that sounds when CO is detected. In addition, the gel tends to accumulate CO over a period of time, resulting in a tendency for false alarms after prolonged exposure to urban pollution.

The third type of detector uses a fuel-cell type electrochemical sensor. These detectors are battery-powered and are much more accurate and responsive to the presence of CO.

The electrolytic cell of an electrochemical sensor must have at least two electrodes. One electrode is the electrode that comes in contact with the gas that is to be detected, and is usually referred to as the sensing electrode. A second electrode is known as the counter electrode or auxiliary electrode. When the gas to be detected comes in contact with the sensing electrode, an oxidation reaction takes place at the sensing electrode, with a corresponding reduction reaction occurring at the counter electrode.

The potential of the sensing electrode must be sufficiently positive so that CO will be oxidized. However, the potential of the sensing electrode is subject to change, because the use of a fixed external voltage bias inter-relates the potential of the sensing electrode to the potential of the counter electrode. The potential of the counter electrode is unstable if the electrode material is not electrochemically reversible, i.e. the exchange current density is not high enough compared with the current passing through the cell. Consequently, it is possible that the potential of the sensing electrode will shift to a value where CO is not fully oxidised at the sensing electrode.

Thus, it can be important to have an electrode with a constant or almost constant potential throughout the reaction. Such an electrode is called the reference electrode and its main role is to stabilize the potential of the sensing electrode. In that event, the potential of the sensing electrode will remain relatively stable so that CO may be quantitatively oxidized.

Other detectors use only two electrodes. In such detectors, the reference electrode also serves as the counter electrode. Any current generated by the sensing electrode passes through this reference/counter electrode.

CO sensors using electrochemically reversible materials such as lead dioxide ($PbO_2$) and silver as reference electrodes show high sensitivity to the presence of CO and a wide linear response range, from below 5 ppm to over 10% v/v. The sensors are robust and reliable, and may be used under demanding conditions e.g. analysing stack gases from industrial plants, monitoring toxic gas concentrations in omissions from a gas producing process and the like. However, such sensors generally require two or more hours for the background current to stabilize, because an initial $O_2/H_2O$ redox coupling reaction controls the reference potential. The sensors have a moderate sensor life, generally of less than 2 years, and tend to be bulky in order to hold sufficient sulphuric acid solution required for operation of the sensor.

An example of a two-electrode sensor is described in U.S. Pat. No. 3,775,125 and examples of three-electrode sensors are described in U.S. Pat. Nos. 4,587,003, 5,284,566 and 5,338,429. In all of these sensors, a platinum/air/water electrode was used as reference electrode. However, such sensors have a number of disadvantages, including (a) high cost due to the use of precious metals e.g. platinum foils and wires, (b) the requirement of strict performance criteria in contact between electrodes and precious metals, and high failure rates due to poor contact, (c) leakage of electrolyte after long periods of operation, (d) costs of assembly of numerous parts of the sensor, and (e) large piece-to-piece variations in sensor output.

SUMMARY OF THE INVENTION

An improved two-electrode electrochemical gas sensor for the detection of CO and other gases has now been found.

Accordingly, an aspect of the present invention provides an electrochemical sensor for detection of a gas in an atmosphere containing the gas, said sensor comprising a housing having an electrochemical gas sensor cell with an electrolyte and first and second electrodes bonded to conductive plastic, each of said first and second electrodes being a membrane formed from a fluoropolymer film having a layer adhered thereto of a catalyst-impregnated fluoropolymer, said layers of each of said first and second electrodes being bonded to conductive plastic, said layers of said first and second electrodes being separated by an absorbent material having an electrolyte absorbed therein, said absorbent material extending between conductive plastic bonded to the layer of the first electrode and conductive plastic bonded to the layer of the second electrode and being in fluid flow communication with a reservoir of said electrolyte, the conductive plastic bonded to said first and second electrodes being connected to means for detection of current passing through said electrodes.

In a preferred embodiment of the present invention, the membrane is a gas permeable membrane or preferably a porous membrane.

In another embodiment, the gas is CO and the electrolyte is sulphuric acid.

In yet another embodiment, electrical connections to the conductive plastic are external to said housing, and the sensor has a leak-proof sealed housing.

In further embodiment, the housing has a chamber in fluid communication with the atmosphere, the membrane of the first electrode forming part of the chamber, preferably with the chamber being separated from the atmosphere by a membrane, especially a gas permeable membrane. The chamber may contain carbon pellets.

In yet another embodiment, the electrodes are formed by depositing a mixture of platinum black powder and a suspension of a fluoropolymer on the fluoropolymer film, and sintering the mixture under pressure onto the fluoropolymer film.

In still another embodiment, the housing is formed from a polyolefin, especially polypropylene or high density polyethylene, and the conductive plastic is polyolefin, especially polypropylene or high density polyethylene, having a filler of carbon black or graphite.

BRIEF DESCRIPTION OF THE DRAWINGS

The present invention is illustrated by the embodiments shown in the drawings, in which:

FIG. 2 is a schematic representation of an embodiment of the sensor in exploded partial cut-away form;

FIG. 3 is a schematic representation of an embodiment of the sensor assembly, in an exploded perspective view;

DETAILED DESCRIPTION OF THE INVENTION

Figure 1:
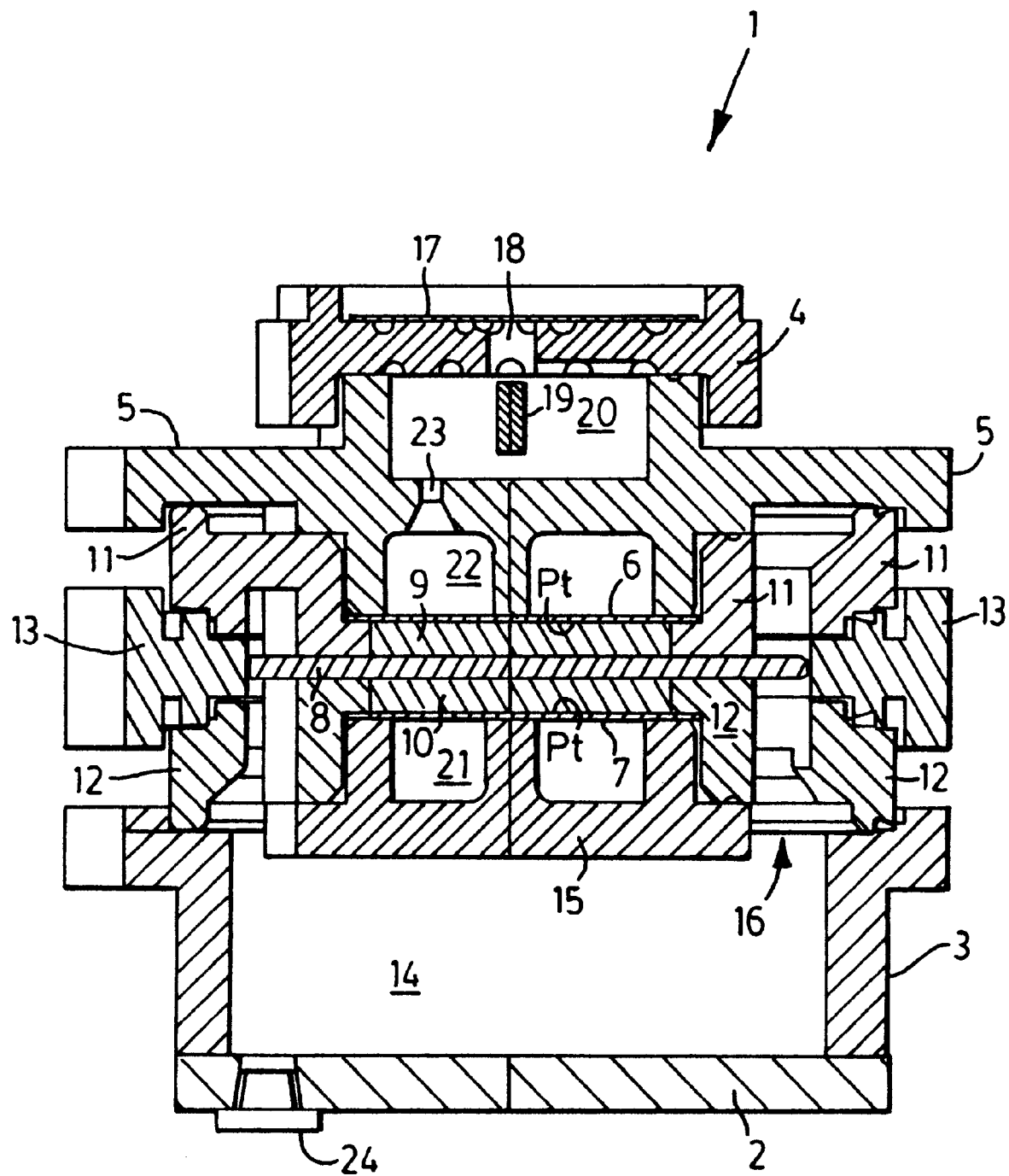
FIG. 1 is a schematic representation of a sensor of the present invention.

FIG. 1 shows a gas sensor, generally indicated by 1. On one of its ends, gas sensor 1 has reservoir cover 2 that fits on reservoir housing 3, whereas on the opposed end gas sensor 1 has scrubber cap 4 that fits over scrubber housing 5. Intermediate between the opposed ends of gas sensor 1 are sensing electrode 6 and counter electrode 7.

Sensing electrode 6 and counter electrode 7 are separated, in sequence, by sensing electrode absorbent pad 9 (which contacts sensing electrode 6), absorbent pad 8 and counter electrode absorbent pad 10 (which contacts counter electrode 7). Absorbent pad 8 extends for a substantial part of the width of the sensor, effecting separation between sensing electrode current collector 11 and counter electrode current collector 12. At the ends of absorbent pad 8, sensing electrode current collector 11 and counter electrode current collector 12 are further separated by current separator 13, current separator 13 being electrically non-conductive. Sensing electrode current collector 11 extends inwardly in contact with absorbent pad 8 to contact the edge of sensing electrode absorbent pad 9. In doing so, sensing electrode current collector 11 contacts the face of sensing electrode 6 and, as discussed below, is bonded to the active layer of sensing electrode 6. In a similar manner, counter electrode current collector 12 extends inwardly in contact with absorbent pad 8 to contact the edge of counter electrode 10, contacting the face of counter electrode 7 and being bonded to the active layer thereof.

Sensing electrode current collector 11, counter electrode current collector 12 and current separator 13 all extend to and form part of the external housing of gas sensor 1. The external housing is also formed by the exterior walls of reservoir cover 2, reservoir housing 3, scrubber cap 4 and scrubber housing 5. As discussed below, reservoir cover 2 and reservoir housing 3 may be unitary i.e. be one part in which case reservoir cover 2 would have plug 24 therein.

As discussed herein, sensing electrode 6 is bonded to sensing electrode current collector 11. Likewise, counter electrode 7 is bonded to counter electrode current collector 12. Such bonding of the electrodes to the electrode current collectors seals gas sensor 1, and in particular separates liquid electrolyte from scrubber housing 5.

Reservoir housing 3 contains reservoir 14. Reservoir 14 is separated, in part, from counter electrode 7 by reservoir separator 15, which forms counter electrode chamber 21 on the side of counter electrode 7 opposed to the absorbent pads. However, reservoir 14 is in fluid flow communication with absorbent pad 8 through wick. Wick 16 is an integral part of absorbent pad 8, and extends downward into reservoir 14. Reservoir cover 2 has plug 24 therein, for use in filling of reservoir 14 with electrolyte. It is understood that in a less preferred embodiment, reservoir cover 2 could be used without a plug 24, and be adapted for assembly onto the sensor after reservoir 14 is filled with electrolyte i.e. be adapted to be screwed or otherwise attached to reservoir housing 3, but it is preferred that reservoir cover 2 and reservoir housing 3 be unitary.

Scrubber cap 4 has gas permeable membrane 17 thereon, which covers gas passage. Within scrubber housing 5 is scrubber chamber 20, which has scrubber baffle 19 located juxtaposed to gas passage 18. Scrubber chamber 20 is connected to sensing electrode chamber 22, through capillary 23, sensing electrode chamber 22 having sensing electrode 6 as a wall thereof.

FIG. 2 shows the gas sensor in an exploded view. Scrubber cap 4 has gas permeable membrane 17 thereon. The underside, as illustrated, of scrubber cap 4, fits over scrubber housing 5, which in turn mates with sensing electrode current collector 11. Sandwiched in between scrubber housing 5 and sensing electrode current collector 11 is sensing electrode 6. Current separator 13, which is electrically non-conductive, separates sensor electrode current collector 11 from counter electrode current collector 12. In addition, between sensing electrode 6 and counter electrode 7 are located sensing electrode absorbent pad 9, absorbent pad 8 and counter electrode absorbent pad 10. Counter electrode 7 is sandwiched between counter electrode current collector 12 and reservoir separator 15. Reservoir housing 3 fits over reservoir separator 15.

FIG. 3 shows an embodiment of the sensor in an exploded perspective view, showing the interrelationship on the parts of the sensor. In the particular embodiment of FIG. 3, pad 28 is in the form of an absorbent pad and a wick, described previously as 8 and 16 respectively in FIG. 1, which are integrally formed together, and adapted to extend into reservoir 14.

Figure 4:
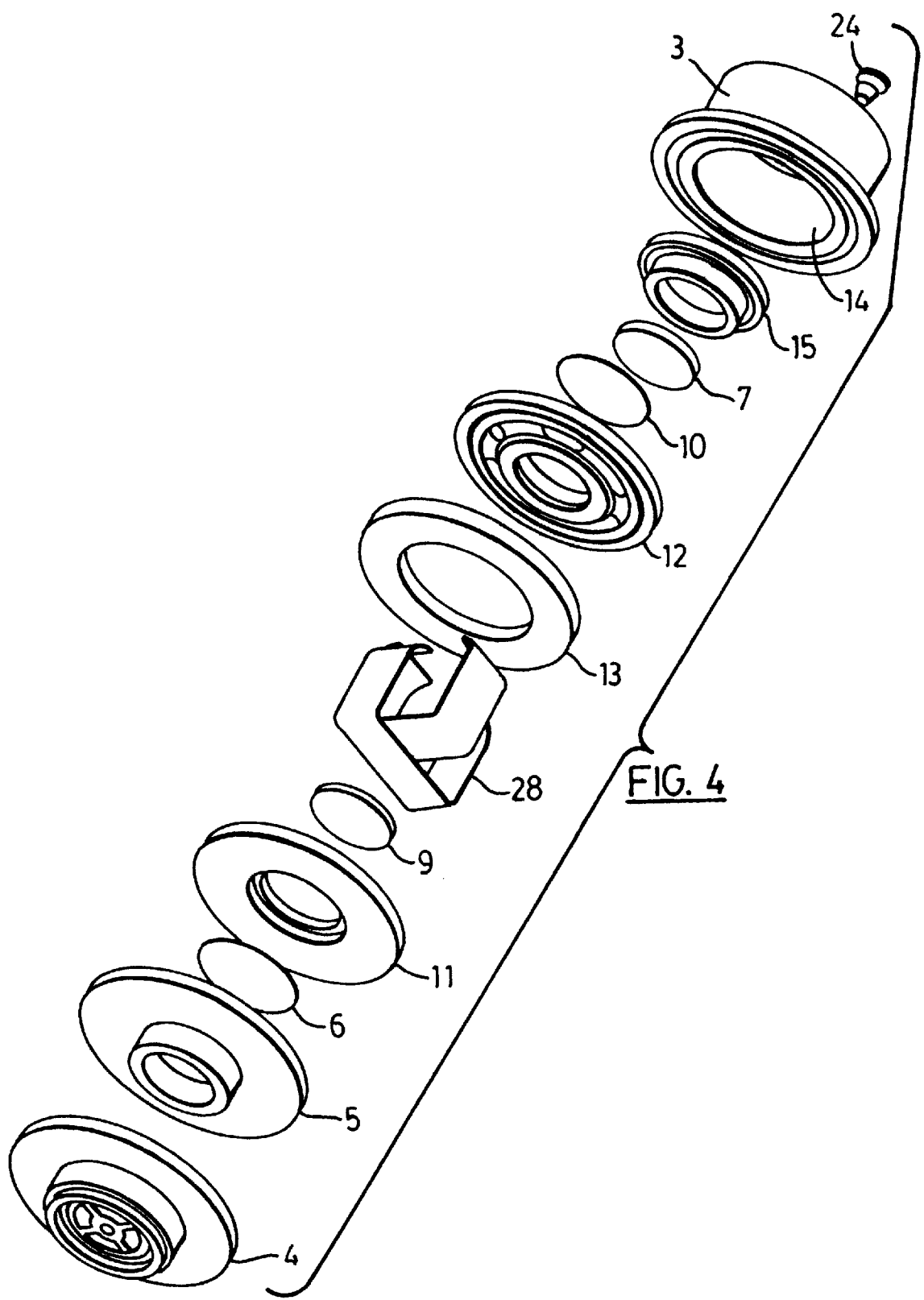
FIG. 4 is a schematic representation, in exploded view, of the scrubber assembly.

FIG. 4 shows the scrubber assembly in exploded view. Gas permeable membrane 17 fits into scrubber cap 4. Scrubber baffle 19 is located under scrubber cap 4 and fits into scrubber housing 5. Sensing electrode 6 fits between sensing electrode current collector 11 and scrubber housing 5, forming sensing electrode chamber 22 that is in fluid communication with scrubber chamber 20.

The gas sensor is illustrated in FIGS. 1–4 in the preferred embodiment of being of circular cross-section. Such a cross-section permits ease of manufacture, including ease of fitting parts together and of screwing certain elements, if that should be a desirably part of the method of manufacture. The circular cross-section also results in a compact gas sensor that may easily be located in a desired location.

Gas sensor 1 may be fabricated in modules, which are then assembled to form the gas sensor. The various parts of the gas sensor are bonded together e.g. using ultrasonic welding, in order to effect liquid and gas tight seals to prevent leakage of liquid from the gas sensor and extraneous intrusion of gases into the sensor.

In an example of the method of manufacture, carbon pellets are placed in the scrubber housing and the scrubber cap and membrane are added, and bonded. The sensing electrode is placed in the sensing electrode current collector 11, and then the scrubber housing is added. The resultant sensing electrode assembly is bonded together, preferably by ultrasonic welding. Similarly, the counter electrode is placed in the counter electrode current collector 12, and then the reservoir separator is added. The resultant counter electrode assembly is bonded together, preferably using ultrasonic welding. The sensor may then be assembled by placing the sensing electrode assembly into the counter electrode assembly, with the absorbent pads discussed above and electrically non-conductive current separator 13 located therebetween. This assembly may now be bonded together e.g. using ultrasonic welding. The fluid is added to the reservoir, through the plug in the reservoir cap. The gas sensor is now ready for installation and connection to electronic monitoring means, as will be understood. The gas sensor, when fabricated, should be gas tight to prevent diffusion of gas, especially CO, into the sensor from a path other than the sensing electrode, as diffusion of in particular CO affects the response of the sensor over a period of time.

It is to be understood that sensing electrode 6 is connected to electronic sensing means exterior to the gas sensor through sensing electrode current collector 11. Similarly, counter electrode 7 is connected to electronic monitoring means through counter electrode current collector 12. Both sensing electrode current collector 11 and counter electrode current collector 12 are conductive plastics, as discussed herein, with the result that there are no wire connections from the sensing or counter electrodes through the housing of gas sensor 1 to the electronic monitoring means. Connections to the electronic monitoring means are external to the gas sensor 1, being connected on the external part of sensing electrode current collector 11 and counter electrode current collector 12. This eliminates possible failure of the sensor due to corrosion of or at the location of electrical leads passing through the housing of a gas sensor to connect to the electrodes.

Although sensing electrode 6 and counter electrode 7 could be of different constructions, it is preferred that sensing electrode 6 and counter electrode 7 be of the same construction. Furthermore, it is preferred that sensing electrode 6 and counter electrode 7 be a gas permeable membrane or porous membrane formed from a fluoropolymer film having a layer of a catalyst-impregnated fluoropolymer adhered thereto. Such an electrode may be formed by spraying or otherwise depositing e.g. by silk screen printing, a mixture of platinum black powder and a suspension of a fluoropolymer onto a fluoropolymer film. An example of a porous membrane is a Mitex™ PTFE membrane from Millipore Co. with a thickness of 125 microns, a porosity of 60% and a mean pore diameter of 5 microns, other membranes being known to those skilled in the art. Subsequently, the mixture of platinum black and fluoropolymer is sintered onto the fluoropolymer film. This may be accomplished by applying both heat and pressure to the coating of platinum black and fluoropolymer on the fluoropolymer film, so that the mixture is sintered and is adhered to the film.

The resultant layer of catalyst-impregnated fluoropolymer on the fluoropolymer film is adhered directly onto the conductive plastic that forms the sensing and counter electrode current collectors. The conductive plastic is formed from a polyolefin, especially polypropylene or high density polyethylene. The conductive plastic has a filler of carbon black or graphite in an amount that provides electrical conductive properties to the plastic. In embodiments, the conductive plastic contains up to 30% by weight of carbon black or graphite powder, and has a specific resistance of about 50–100 ohms/cm. The sensing and counter electrodes may be bonded to the sensing and counter electrode current collectors using ultrasonic welding, although other electrical means of bonding the layer to the housing may be used.

In the preferred embodiment of FIG. 1, a gas permeable membrane is placed across gas passage 18 in scrubber cap 4. The membrane, 17, which is preferably a gas permeable membrane but may be a gas porous membrane, is intended to prevent contamination of the sensor by particulates, aerosols and other organic or high molecular weight molecules as a consequence of the flow of ambient atmospheric air directly into scrubber chamber 4, evaporation of the reservoir liquid from the sensor and reduce effects of pressure fluctuations and air turbulence on the gas sensor. It has been found that use of a gas permeable membrane may increase the response time of the sensor to the presence of CO. For instance, in a test of an embodiment of the sensor using a membrane that was Teflon™ FEP fluoropolymer film with a nominal thickness of 0.5 mil and obtained from the DuPont Company, the response time increased from less than one minute to 2.5 minutes for an atmosphere with 90 ppm of CO, but tests of another membrane formed from a fluoropolymer film with a polycarbonate backing gave no significant increase in response time. Thus, a membrane may be selected that provides an increase in response time, if any, that is acceptable for the proposed use.

In addition, scrubber chamber 4 preferably contains pellets of carbon to absorb polar gases e.g. $H_2S$ and high molecular weight organic vapours in the atmospheric air and which has passed through the gas permeable membrane 17. These substances poison and degrade the sensing electrode. Membrane 17 is preferably a fluoropolymer membrane.

The sensor of the present invention uses two electrodes. However, the sensing electrode is always exposed to the ambient atmosphere, whereas the counter electrode is isolated. The counter electrode is conveniently an air/water reference electrode since its potential is governed by the redox couple of oxygen/water. The operating oxygen comes from the atmosphere and becomes dissolved in the electrolyte. Any carbon monoxide that reaches the sensor will be fully converted to carbon dioxide ($CO_2$) at the sensing electrode site. The net reaction in the cell is the conversion of CO to $CO_2$ and no substance in the sensor is consumed. Thus, the sensor will not degrade after long-term exposure to CO.

A typical gas diffusion electrode contains high surface area catalysts such as platinum black and a hydrophobic binder, usually fine particles of fluoropolymer e.g. particles of Teflon™ fluoropolymer. Electron microscopic examination of the fluoropolymer-bonded platinum black electrode showed that the platinum black formed loosely packed aggregates interspersed with fluoropolymer particles and threads, the threads binding the material into a mechanically secure structure. When a hydrophilic catalyst is wetted by electrolyte, the hydrophobic binder remains dry, providing gas paths throughout the depth of the electrode. The liquid films around the catalyst particles are so thin that the gas diffusion path is greatly shortened. Hence, highly efficient gas diffusion electrodes are obtained. The loading of platinum black ranges from 1 to 20 mg/cm$^2$. The loading of fluoropolymer binder ranges from 5% to 40% by weight.

The present invention has been described herein with reference to reservoir 14 being in fluid flow communication with absorbent pad 8 through wick 16. However, other means may be provided to connect reservoir 14 to absorbent pad 8 e.g. by providing counter electrode 7 with an orifice therein with a wick extending through the orifice and connecting absorbent pad 8 with reservoir 14.

The various outer parts of the housing, especially of reservoir 14, may be fabricated from polymer that is resistant to sulphuric acid e.g. acrylonitrile-butadiene-styrene (ABS), polyvinyl chloride (PVC) and polyvinylidene difluoride (PVDF) and the like.

For operation, reservoir is charged with sulphuric acid, for example 50% $H_2SO_4$ aqueous electrolyte solution, during assembly of gas sensor 1, although a wide range of concentrations may be used e.g. a range of at least 10–75% (v/v) $H_2SO_4$. The reservoir is preferably packed with an inert material, for instance fibreglass wool, to reduce "sloshing" of liquid in the reservoir during movement of the sensor. Gas sensor 1 is then placed in the location where carbon monoxide is to be monitored, and connected to electronic monitoring means for detection of currents flowing through sensing electrode 6 and counter electrode 7, as will be understood by persons skilled in the art. In the absence of carbon monoxide, the current should be null. When the atmosphere contains carbon monoxide, carbon monoxide permeates through membrane 17 and comes in contact with sensing electrode 6, being oxidised at the sensing electrode and correspondingly producing a current, which is amplified by external electronic means. A microcomputer will then compare this signal to a pre-set reference level to determine whether an alarm signal should be issued.

The gas sensor is described herein with particular reference to detection of carbon monoxide. However, it is to be understood that the sensor may be used to detect other gases e.g. hydrogen sulphide ($H_2S$), oxides of nitrogen (NO and $NO_2$), sulphur dioxide ($SO_2$), chlorine and the like. For detection of a specific gas other than carbon monoxide, it might be necessary to remove or replace the scrubber (carbon, pellets) described herein, change the electrode composition and/or set the voltage bias at a different value, as will be understood by persons skilled in the art.

In tests of gas sensors of the invention as described and illustrated herein, it has been found that the response of the sensor is essentially linear at concentrations of CO up to at least about 500 ppm. As illustrated herein, response rate was fast, being 90% of full scale response in about 3 minutes.

The present invention is illustrated by the following examples.

EXAMPLE I

A sensor of the invention was connected to a EG&G Princeton Applied Research Model 263 potentiostat/Galvanostat. The working electrode lead of the instrument was connected to the sensing electrode and the counter and reference electrode leads to the counter electrode. The instrument was set to potentiostat mode and the potential was set to 0.000 V. Sensor responses to carbon monoxide were recorded on a BAS (Bioanalytical Systems) XYT chart recorder.

The sensor was placed in a glass bell jar containing clean air. After recording had commenced, a sample of air having a known and constant concentration of CO was passed through the jar at a flow rate of approximately 1 mL/min.

Figure 6:
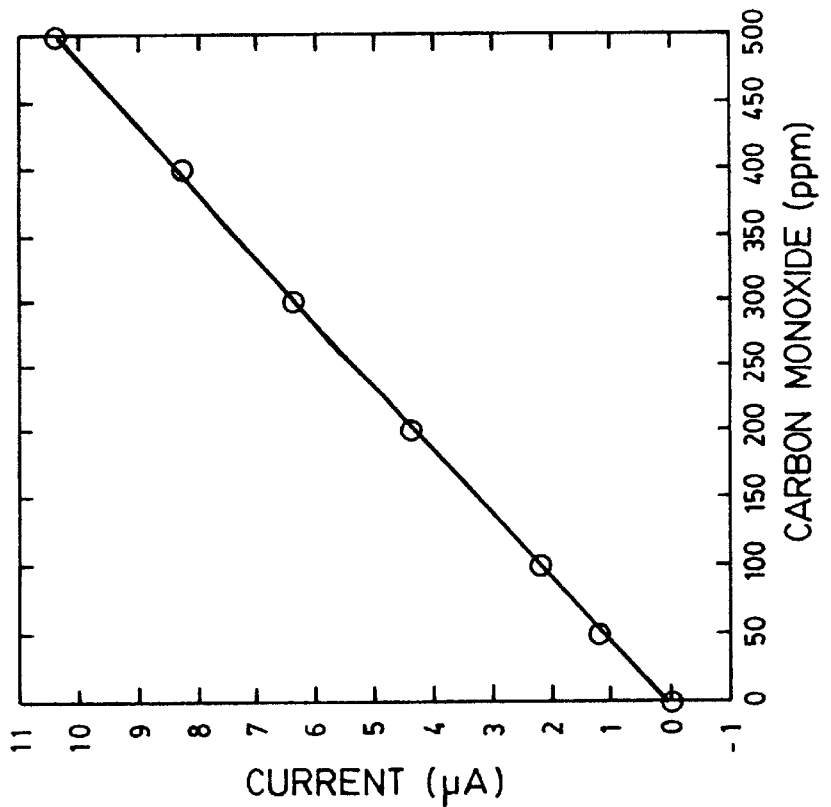
FIG. 6 is a graphical representation of current v CO concentration.
Figure 5:
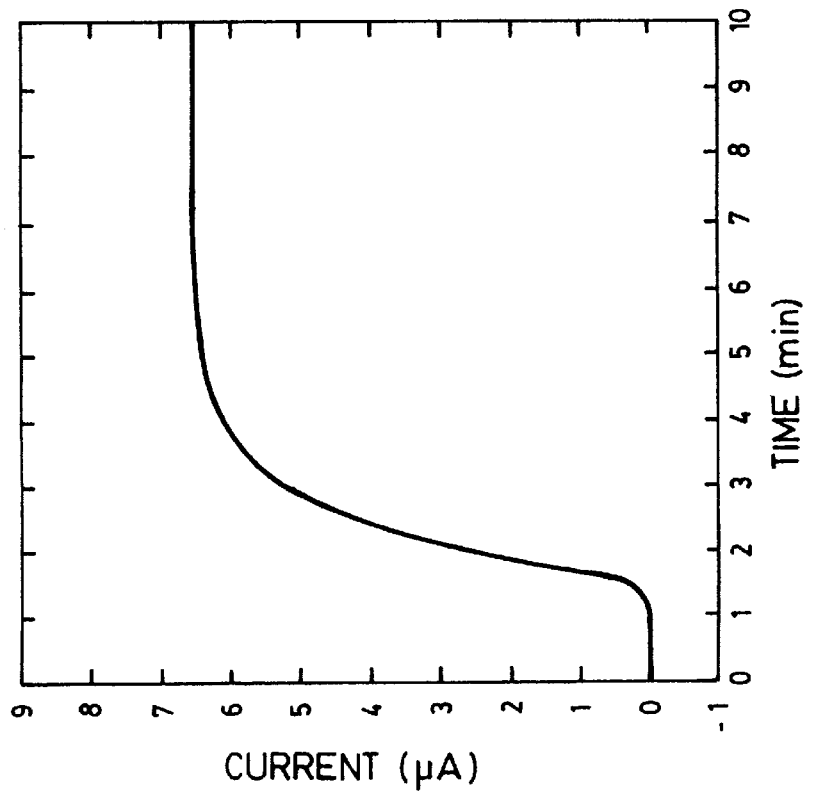
FIG. 5 is a graphical representation of current v time in sensing of CO.

The results obtained are shown graphically in FIG. 5 and FIG. 6.

EXAMPLE II

A sensor of the invention was connected to an operational amplifier with a potentiometer as feedback resistor. The sensing electrode was connected to the inverting input and the counter electrode was connected to the non-inverting input. Sensor output was monitored by a digital voltmeter. The potentiometer had been adjusted to give a reading of 200 mV when the sensor was exposed to 200 ppm carbon monoxide.

The results showed that in clean air, air not containing carbon monoxide, the sensor output was 0.7 mV. When the concentration of carbon monoxide was 10 ppm, the reading was 8 mV, whereas at concentrations of 100 ppm and 400 ppm of carbon monoxide, the readings were 103 mV and 374 mV, respectively.

EXAMPLE III

Charcoal was removed from the scrubber housing and a sensor of the present invention was used to detect the presence of hydrogen sulphide ($H_2S$). The sensor was connected to PAR Potentiostat Model 263 and had the same set-up as in Example I. The sensor showed a linear response to $H_2S$ in the range of 0 to 50 ppm and the sensitivity to the presence of hydrogen sulphide was several times higher than for CO.

The following data were obtained.

| Concentration of $H_2S$ (ppm) | Sensor response ($\mu A$) |
| --- | --- |
| 0 | −0.05 |
| 2.5 | 0.4 |
| 8 | 1.25 |
| 25 | 4.2 |
| 50 | 8 |

The examples illustrate the use of the sensor in the detection of two different gases.

The gas sensor of the present invention provides for monitoring of the presence of a number of gases, especially CO, using a compact sealed sensor that is not susceptible to adverse affects of wires passing through the housing of the sensor. The invention also provides a cost effective and more reliable sensor for the toxic gas detector market. The sensor is particularly intended for domestic use in monitoring low levels of carbon monoxide, but it may be used in other uses. The two electrode configuration greatly simplifies the sensor design and makes possible the use of conductive plastics instead of platinum as current collector. It is also believed that the sensor is superior to other models in terms of life and reliability.

In contrast, known sensors with metal pins usually have welded platinum wires/foils to make contact with electrodes, as a consequence of the nature of the electrolyte that is used. These wires or foils tend to be so thin that a good electrical connection cannot be guaranteed, and the connection tends to be vulnerable and fragile, too. In addition, because metals and plastics have totally different heat expansion coefficients, such sensors tend to leak electrolyte after exposure to significantly different temperatures. The leakage of electrolytes can significantly effect sensor performance and shorten the sensor life. It is believed that these problems have been avoided or alleviated in the sensor of the invention.

What is claimed is:

1. An electrochemical gas sensor for detection of a gas in an atmosphere containing the gas, said sensor comprising a leak-proof sealed housing formed at least in part from a first conductive plastic member, a second conductive plastic member and a plurality of non-conductive plastic members, the housing containing a fluid electrolyte and a first electrode having a periphery sandwiched between said first conductive plastic member and one of said non-conductive plastic members, and a second electrode having a periphery sandwiched between said second conductive plastic member and another of said non-conductive plastic members, each of said first and second electrodes comprising a membrane formed from a fluoropolymer film having a layer adhered thereto of a catalyst-impregnated fluoropolymer, said layer of each of said first and second electrodes being bonded to the respective first and second conductive plastic members, said layers of said first and second electrodes being separated by an absorbent material having said fluid electrolyte absorbed therein, said absorbent material extending between the first conductive plastic member bonded to the layer of the first electrode and the second conductive plastic member bonded to the layer of the second electrode, the absorbent material being in fluid flow communication with a reservoir of said fluid electrolyte, the first and second conductive plastic members bonded to said first and second electrodes being connected to means for detection of current passing through said electrodes.

2. The apparatus of claim 1 in which each of the first and second electrodes comprises a gas permeable membrane.

3. The apparatus of claim 1 in which each of the first and second electrodes comprises a porous membrane.

4. The apparatus of claim 3 in which electrical connections to said first and second conductive plastic members are external to said housing.

5. The apparatus of claim 4 in which the electrodes are formed by depositing a mixture of platinum black powder and a suspension of a fluoropolymer on the fluoropolymer film, and sintering the mixture under pressure onto the fluoropolymer film.

6. The apparatus of claim 5 in which the housing is formed from a polyolefin.

7. The apparatus of claim 6 in which the polyolefin is polypropylene or high density polyethylene.

8. The apparatus of claim 4 in which the first and second conductive plastic members are polyolefin.

9. The apparatus of claim 8 in which the polyolefin is polypropylene or high density polyethylene.

10. The apparatus of claim 4 in which the first and second conductive plastic members have a filler of carbon black or graphite.

11. The apparatus of claim 4 in which the housing has a chamber in fluid communication with the atmosphere, said membrane of said first electrode forming part of the chamber.

12. The apparatus of claim 11 in which the chamber contains carbon pellets.

13. The apparatus of claim 11 in which said chamber is separated from the atmosphere by a membrane.

14. The apparatus of claim 13 in which said chamber is separated from the atmosphere by a gas permeable membrane.

15. The apparatus of claim 4 in which the gas to be detected is carbon monoxide.

16. The apparatus of claim 4 in which the housing is formed from polypropylene and the conductive plastic members are formed from polypropylene having a filler of carbon-black.

17. The apparatus of claim 4 in which the first and second conductive plastic members are bonded to the said layer of said first and second electrodes by welding.

18. The apparatus of claim 1 in which the catalyst is platinum and the electrolyte is aqueous sulphuric acid solution.

* * * * *